United States Patent
Robison et al.

(10) Patent No.: US 7,244,263 B2
(45) Date of Patent: Jul. 17, 2007

(54) SURGICAL INSTRUMENT

(75) Inventors: Braden Robison, Fremont, CA (US); Alan Ackley, Silverado, CA (US)

(73) Assignee: Stryker Corporation, Kalamazoo, MI (US)

( * ) Notice: Subject to any disclaimer, the term of this patent is extended or adjusted under 35 U.S.C. 154(b) by 914 days.

(21) Appl. No.: 10/119,342

(22) Filed: Apr. 9, 2002

(65) Prior Publication Data

US 2003/0191488 A1 Oct. 9, 2003

(51) Int. Cl.
*A61B 17/32* (2006.01)
*A61B 17/20* (2006.01)

(52) U.S. Cl. .................. 606/170; 606/180; 604/22

(58) Field of Classification Search ........ 606/170–171, 606/174, 180; 285/221, 138.1, 145.1; 604/22
See application file for complete search history.

(56) References Cited

U.S. PATENT DOCUMENTS

| | | | |
|---|---|---|---|
| 412,920 A | 10/1889 | Hood et al. | |
| 2,093,682 A | 9/1937 | Levy | |
| 2,921,585 A | 1/1960 | Schumann | |
| 3,613,052 A * | 10/1971 | Maltais | 439/872 |
| 4,071,029 A | 1/1978 | Richmond et al. | |
| 4,210,146 A | 7/1980 | Banko | |
| 4,445,509 A | 5/1984 | Auth | |
| 4,466,429 A | 8/1984 | Loscher et al. | |
| 4,497,320 A | 2/1985 | Nicholson et al. | |
| 4,576,772 A | 3/1986 | Carpenter | |
| 4,603,694 A | 8/1986 | Wheeler | |
| 4,646,738 A | 3/1987 | Trott | |
| 4,678,459 A | 7/1987 | Onik et al. | |
| 4,696,667 A | 9/1987 | Masch | |
| 4,728,319 A | 3/1988 | Masch | |
| 4,735,605 A | 4/1988 | Swartz | |
| 4,815,462 A | 3/1989 | Clark | |
| 4,858,897 A | 8/1989 | Irifune | |
| 4,883,458 A | 11/1989 | Shiber | |
| 4,886,490 A | 12/1989 | Shiber | |
| 4,911,148 A | 3/1990 | Sosnowski et al. | |
| RE33,258 E | 7/1990 | Onik et al. | |
| 4,979,939 A | 12/1990 | Shiber | |
| 4,990,134 A | 2/1991 | Auth | |
| 4,998,527 A | 3/1991 | Meyer | |
| 5,041,082 A | 8/1991 | Shiber | |
| 5,135,481 A | 8/1992 | Nemeh | |
| 5,135,531 A | 8/1992 | Shiber | |
| 5,152,744 A | 10/1992 | Krause et al. | |
| 5,269,785 A | 12/1993 | Bonutti | |
| 5,269,798 A | 12/1993 | Winkler | |

(Continued)

FOREIGN PATENT DOCUMENTS

AU B-60751/94 11/1994

(Continued)

*Primary Examiner*—Michael J. Hayes
*Assistant Examiner*—M. Thomas Andersen
(74) *Attorney, Agent, or Firm*—Flynn, Thiel, Boutell & Tanis, P.C.

(57) ABSTRACT

A surgical instrument, suitable for endoscopic surgery has a first member and a movably driven second member movable in such first member. One such member comprises a generally tubular proximal member and a tissue working tip which are relatively telescoped and have opposed surfaces. A projection protrudes from such tip surface through such generally tubular member surface to fixedly secure same together.

37 Claims, 14 Drawing Sheets

U.S. PATENT DOCUMENTS

| | | | |
|---|---|---|---|
| 5,282,821 A | 2/1994 | Donahue | |
| 5,285,795 A | 2/1994 | Ryan et al. | |
| 5,286,253 A | 2/1994 | Fucci | |
| 5,312,399 A | 5/1994 | Hakky et al. | |
| 5,320,635 A | 6/1994 | Smith | |
| 5,322,505 A | 6/1994 | Krause et al. | |
| 5,376,078 A | 12/1994 | Dinger, III et al. | |
| 5,411,514 A | 5/1995 | Fucci et al. | |
| 5,437,630 A | 8/1995 | Daniel et al. | |
| 5,437,660 A | 8/1995 | Johnson et al. | |
| 5,510,070 A | 4/1996 | Krause et al. | |
| 5,527,104 A * | 6/1996 | Moss | 312/264 |
| 5,529,580 A | 6/1996 | Kusunoki et al. | |
| 5,532,428 A * | 7/1996 | Radloff et al. | 174/35 GC |
| 5,540,702 A | 7/1996 | Walz | |
| 5,540,708 A * | 7/1996 | Lim et al. | 606/170 |
| 5,593,416 A | 1/1997 | Donahue | |
| 5,601,583 A | 2/1997 | Donahue et al. | |
| 5,601,586 A | 2/1997 | Fucci et al. | |
| 5,620,415 A | 4/1997 | Lucey et al. | |
| 5,620,447 A | 4/1997 | Smith et al. | |
| 5,643,294 A | 7/1997 | Tovey et al. | |
| 5,643,303 A | 7/1997 | Donahue | |
| 5,665,101 A | 9/1997 | Becker et al. | |
| 5,690,660 A | 11/1997 | Kauker et al. | |
| 5,707,350 A | 1/1998 | Krause et al. | |
| 5,749,885 A | 5/1998 | Sjostrom et al. | |
| 5,755,731 A | 5/1998 | Grinberg | |
| 5,766,200 A | 6/1998 | Mazurek et al. | |
| 5,782,834 A | 7/1998 | Lucey et al. | |
| 5,782,848 A | 7/1998 | Lennox | |
| 5,792,167 A | 8/1998 | Kablik et al. | |
| 5,807,241 A | 9/1998 | Heimberger | |
| 5,817,034 A * | 10/1998 | Milliman et al. | 600/566 |
| 5,833,692 A | 11/1998 | Cesarini et al. | |
| 5,851,208 A | 12/1998 | Trott | |
| 5,921,956 A | 7/1999 | Grinberg et al. | |
| 5,922,003 A | 7/1999 | Anctil et al. | |
| 5,928,257 A | 7/1999 | Kablik et al. | |
| 5,947,990 A | 9/1999 | Smith | |
| 5,957,881 A | 9/1999 | Peters et al. | |
| 5,961,532 A * | 10/1999 | Finley et al. | 606/170 |
| 6,007,556 A | 12/1999 | Kablik et al. | |
| 6,132,448 A | 10/2000 | Perez et al. | |
| 6,342,061 B1 | 1/2002 | Kauker et al. | |
| RE38,018 E * | 3/2003 | Anctil et al. | 606/170 |
| 6,620,180 B1 * | 9/2003 | Bays et al. | 606/171 |
| 6,790,221 B2 * | 9/2004 | Monroe et al. | 623/1.11 |
| 6,899,712 B2 * | 5/2005 | Moutafis et al. | 606/49 |

FOREIGN PATENT DOCUMENTS

| | | |
|---|---|---|
| CA | 2 123 015 | 11/1994 |
| DE | 38 28 478 A1 | 5/1989 |
| DE | 3828478 A1 * | 5/1989 |
| EP | 445 918 B1 | 9/1991 |
| EP | 481 760 A1 | 4/1992 |
| EP | 592 249 A2 | 4/1994 |
| EP | 609 084 A2 | 8/1994 |
| EP | 613 661 A3 | 9/1994 |
| EP | 623 317 A1 | 11/1994 |
| EP | 669 105 A3 | 8/1995 |
| EP | 677 276 A1 | 10/1995 |
| EP | 0 393 834 B1 | 5/1996 |
| GB | 1 235 321 | 6/1971 |
| JP | 61-265133 | 11/1986 |
| JP | 6-327692 | 11/1994 |
| WO | WO92/08416 | 5/1992 |
| WO | WO93/04634 | 3/1993 |
| WO | WO98/49953 | 11/1998 |

* cited by examiner

FIG. 2
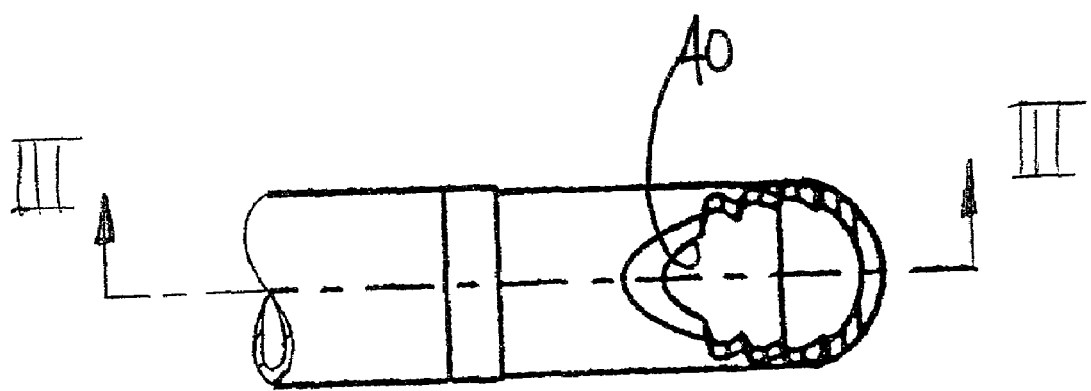
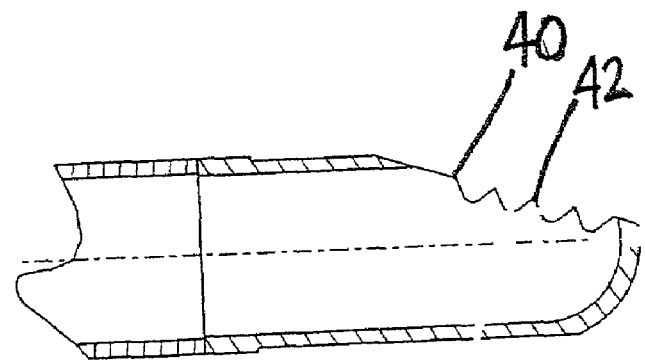
FIG. 3

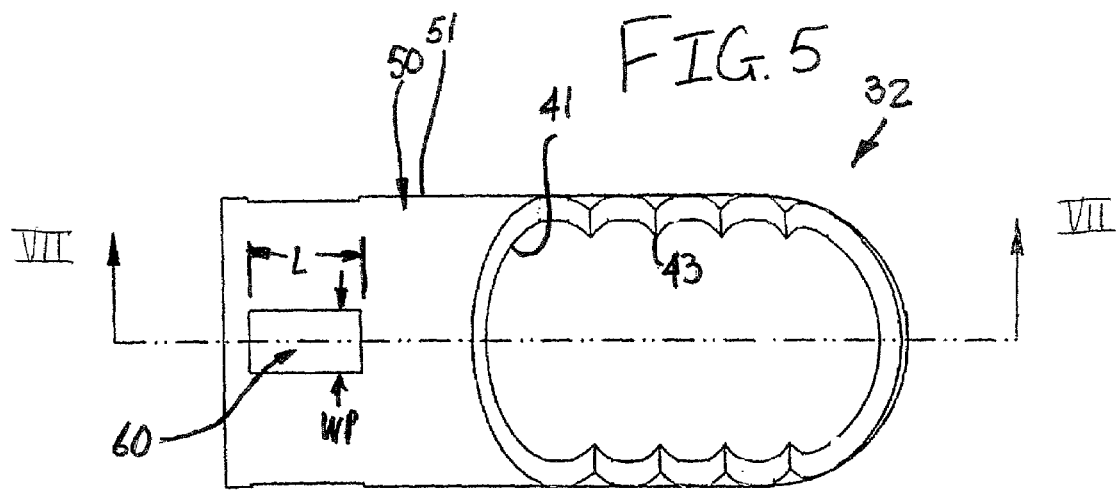
FIG. 5
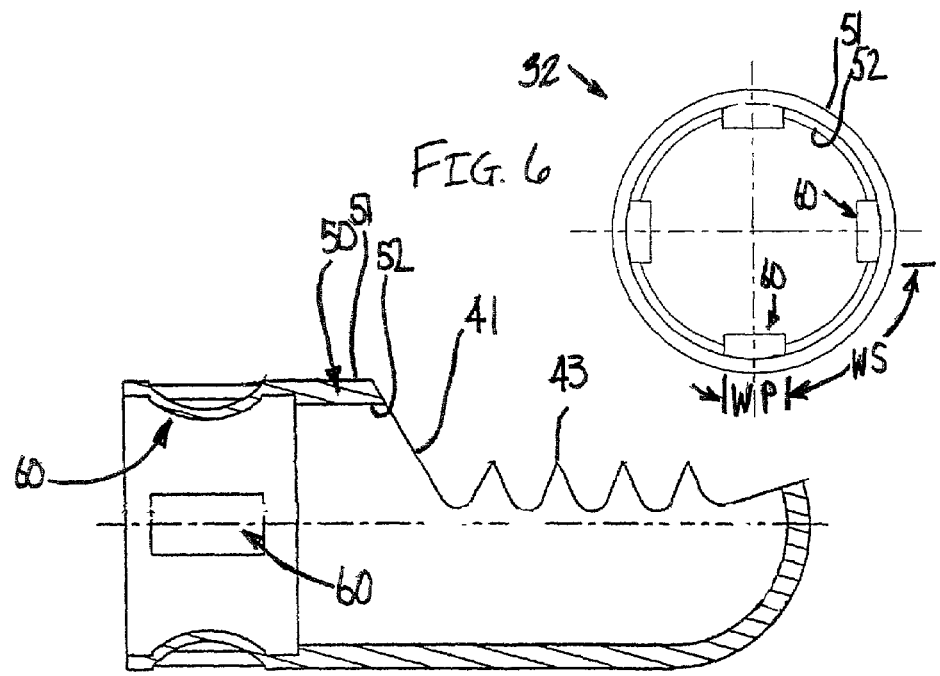
FIG. 6
FIG 7

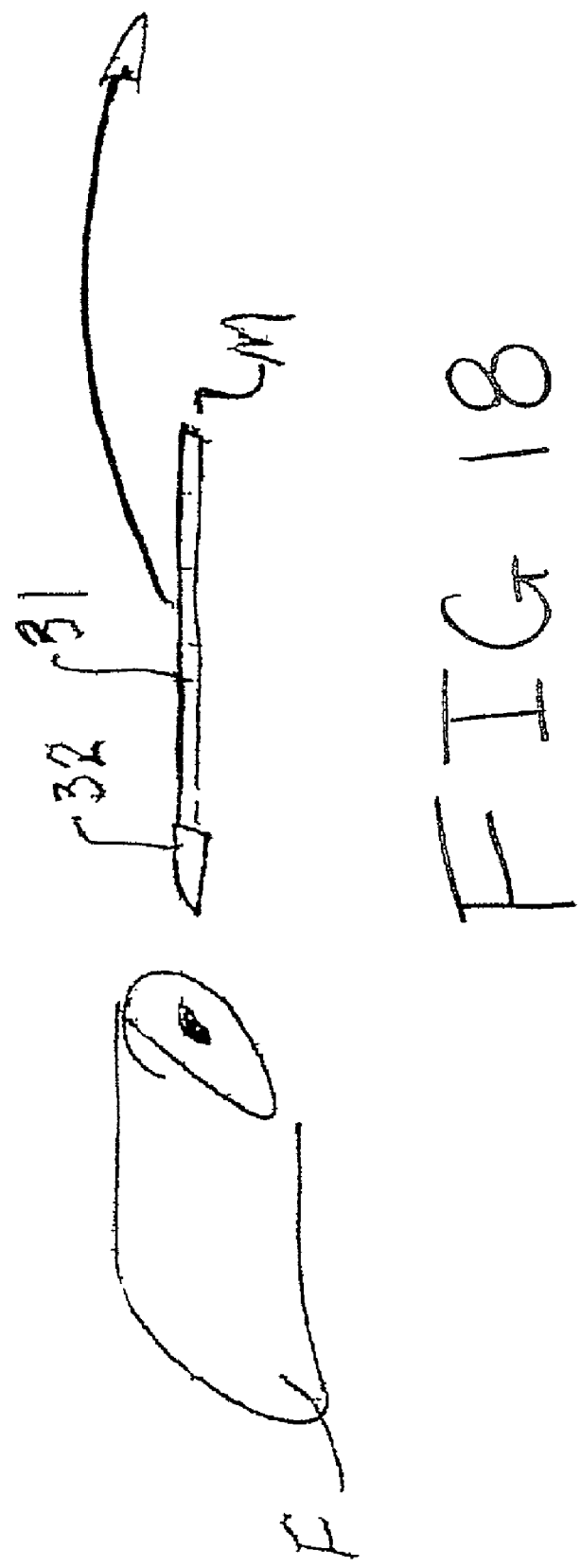

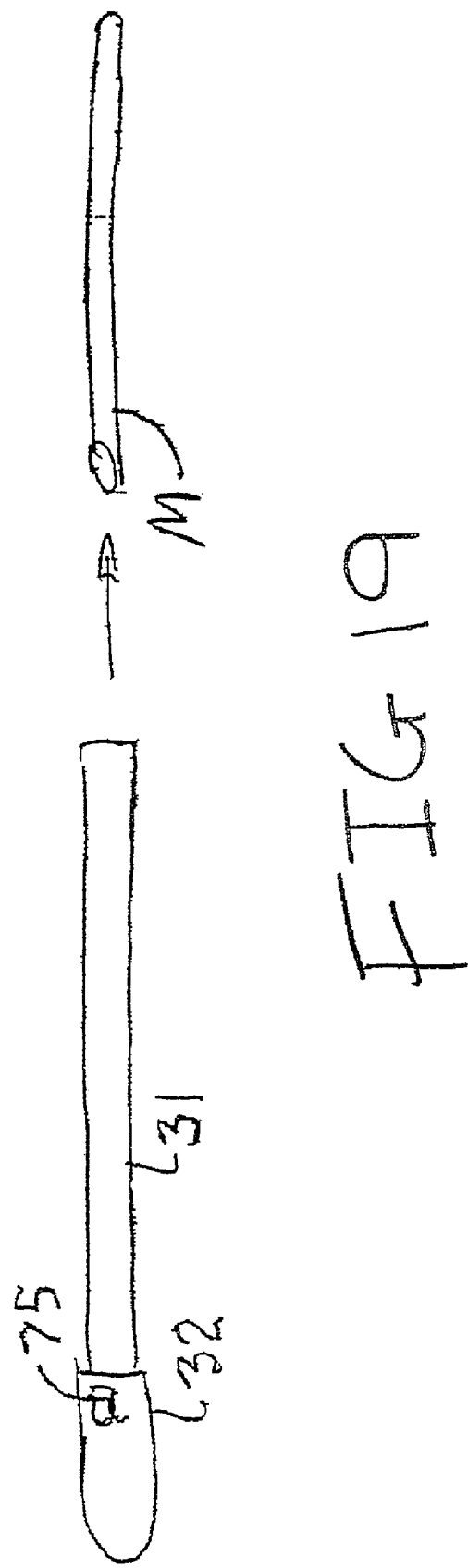

SURGICAL INSTRUMENT

FIELD OF THE INVENTION

This invention relates to a surgical instrument usable for endoscopic surgery and having an outer member and an inner member movable in the outer member.

BACKGROUND OF THE INVENTION

Prior tissue working instruments, suitable for endoscopic surgery, have included a hand piece engagable proximal part and a tissue working distal part, and more particularly have included an elongate, generally tubular outer member in which an elongate inner member is disposed movably for surgically working (e.g. removing, shaping, etc.) tissue.

Early examples of such instruments tended to be rigid and straight. Later examples included instruments having a bent or bendable outer tubular member and an inner elongate member having a length portion of sufficient flexibility to enable tissue working movement (e.g. rotation and/or reciprocation) thereof within the bent outer member.

Typically the proximal end of the outer member is held fixedly to the frame of a hand piece and the movable inner member is movably (e.g. rotatably or reciprocably) driven by a motor unit fixed to the hand piece housing.

By way of example, some prior instruments of this kind use a movably driven inner member which enables surgical detritus, such as typically liquid carrying bits of severed tissue, to be drawn proximally of the tubular inner member toward a suction source connected to the hand piece.

Instruments of this type include so-called shavers or cutters, wherein the inner and outer members have distal tissue working tips having cutting edges relatively movable to shear tissue from the surgical site. Instruments of this type may further include burs in which an inner member distal end carries a bur head with sharp edges movable (e.g. rotatable) to remove bits of tissue from the surgical site. The bur head may be partially guarded by the distal end of the outer member.

In early bent instruments of this general type, the flexible inner member portion at the outer member bend was variously constructed of an elongate helical metal coil, or counter wound coaxial helical metal coils, or a solid metal tube perforated by transverse slots or spaced holes. Difficulties variously included limited usable operating life, limited durability in use, expense and relative complexity of manufacture, and difficulty of sealing against leakage (e.g. of incoming irrigation liquid or outgoing suctioned material) through the wall of the inner tube flexible portion, as the moving inner member flexed.

In time, leading suppliers in the industry introduced movably driven inner tubular members of intrinsically flexible polymer materials, with or without additional fill (particles, strings, etc.) or reinforcing structure embedded therein.

This gave rise to attempts to fix a metal tissue working tip on the distal portion of the polymer tube to try to transmit sufficient torque.

For example, Donahue U.S. Pat. No. 5,282,821 bonds (by adhesive) a cutting tip to a rotor tube which may be of plastic. See also Ryan U.S. Pat. No. 5,282,795 which discloses a reciprocating cutter.

Lim et al. U.S. Pat. No. 5,540,708 in FIGS. 9-11 discloses complexly preformed fingers 125 extending proximally from the cutting tip 110 to be received in corresponding preformed recesses in the distal end of the polymer tube 102 to form a mechanical interlock between the tube and tip. However, the forming and/or machining operations required on the adjacent ends of the tip and tube suggest substantial manufacturing expense.

Anctil U.S. Pat. No. 5,922,003 discloses a metal cutting tip having a reduced outer diameter proximal shank with diametrically opposed axially elongate slots 52, 62, 152, 162, 252, 262, etc. (FIGS. 4-7 and 13-15) or diametrically opposed and longitudinally spaced holes 486 (FIG. 16), wherein such cutting tip shank is inserted into the open distal end of a flexible tube 40 of polymer reinforced by wires 68 (FIG. 8). The result is surrounded by heat shrink tubing. The resulting assembly is heated to cause the polymeric material 66 of the tube to flow and the heat shrink tubing to shrink, thereby forcing the polymeric material to flow radially inwardly into the aforementioned slots or holes formed in the tip shank. Axially mechanically interlocking the tip and tube appears to require relatively complex machining to form the diametrically opposed slots or plural holes and thus make the tip relatively expensive. Further, the several embodiments disclosed all show two circumferentially narrow portions of presumably weaker flowed polymer material sandwiched between circumferentially very wide expanses of presumably stronger metal tip material, which may limit the maximum torque transmittable from the tube to the tip.

Finley et al. U.S. Pat. No. 5,961,532 in FIGS. 11-13 shows a metal tip 40 having a reduced outside diameter proximal portion (annular flange) 61, whose outer periphery is deeply knurled, and a polymer tube 32 having a cylindrical recess 62. Prior to assembly, the tip annular flange 61 is heated and then axially telescoped in the polymer tube recess 62, such that the thermoplastic polymer of the tube plastically flows around the hills and into the valleys of the tip knurl to fix the tube to the tip. Optionally, the tube 62 may be coated with an adhesive, such as epoxy resin, prior to such telescoping. This patent is assigned to the Assignee of the present invention and in general has proved successful in use. However, machining is required to form the tube recess 62 and tip knurl 71. For example, the tip annular flange 61 and tube wall bounding the recess 62 must be of sufficient wall thickness and strength, to avoid distortion or breakage in normal use. However, the depth of the knurl (height from hill top to valley) must be big enough to ensure secure fixation to the polymer tube. In one example in which the outside diameter of the instrument outer tubular member was 4 mm, the thickness of the tip annular flange at the bottom of the knurl valleys was 0.0032 inch (about three one-thousandths of an inch). Thus, relatively high machining precision and hence cost may be required, particularly in smaller outside diameter cutters.

Accordingly, objects and purposes of the present invention include providing a surgical instrument avoiding, or at least reducing negatives of prior devices, and which combines relatively low cost of manufacture with successful operation (including a sturdy fixation of a tissue working tip to a motor driven deformable tubular member). Other objects and purposes of the invention will be apparent to persons of ordinary skill in this art upon reading the following description and inspecting the accompanying drawings.

SUMMARY OF THE INVENTION

A surgical instrument, suitable for endoscopic surgery, is of the kind having a first member and a movably driven second member movable in such first member. One such member comprises a generally tubular proximal member and a tissue working tip which are relatively telescoped and have opposed surfaces. A projection protrudes from such tip surface through such generally tubular member surface to fixedly secure same together.

BRIEF DESCRIPTION OF THE DRAWINGS

FIG. 2 is an enlarged fragmentary view of the distal end portion of the outer member of the FIG. 1 instrument, looking downward in FIG. 1.

FIG. 3 is a central cross sectional view substantially taken on the line III-III of FIG. 2.

FIG. 5 is an enlarged view of the distal tip of the FIG. 4 inner member, looking downward in FIG. 4.

FIG. 6 is a proximal end view of the FIG. 5 tip, looking rightward in FIG. 5.

FIG. 7 is a central cross sectional view substantially taken on the line VII-VII of FIG. 5.

FIG. 18 schematically shows the FIG. 17 assembly removed from the FIG. 15 heating fixture.

FIG. 19 schematically shows the FIG. 18 tip and shaft assembly following removal of the mandrel M in FIG. 16.

DETAILED DESCRIPTION

Figure 1:
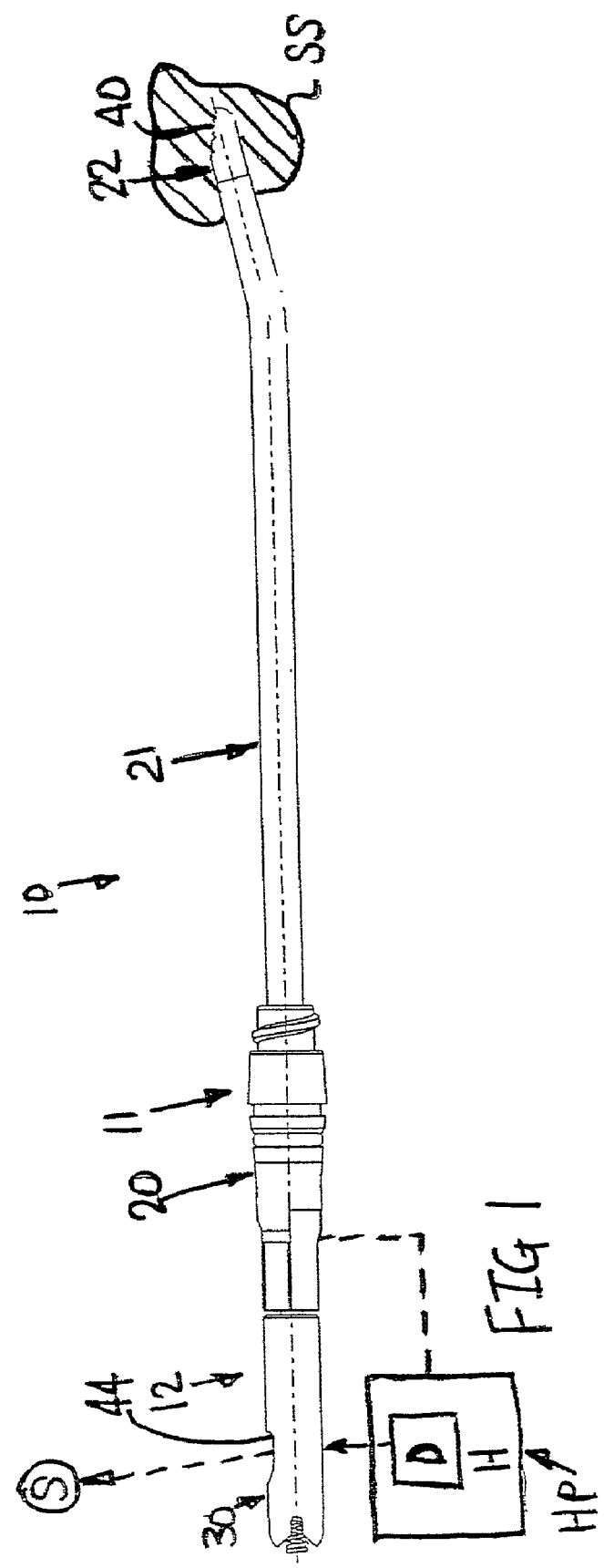
FIG. 1 is a partially schematic, elevational view of a surgical instrument embodying the invention.

A surgical instrument 10 (FIG. 1) embodying the invention comprises an elongate generally tubular outer member 11 and an inner member 12 movably disposed in the outer member 11. In the embodiment shown, the inner member 12 is rotatable in the outer member 11 although other types of relative motion (e.g. reciprocating motion) therebetween are contemplated.

The particular surgical instrument disclosed in FIGS. 1-7, by way of example, is of a type typically referred to as a cutter or shaver. However, it is contemplated that the invention may be embodied in surgical instruments of other types, for example burs or punches or other tissue working surgical instruments. Further, the terms inner and outer applied to the members 11 and 12 are intended to refer to their relative radial position and do not exclude kinds of surgical instruments in which at least one further member may be disposed radially within, without, or between the mentioned inner and outer members.

Turning now more particularly to the particular surgical instrument 10 shown in FIGS. 1-4, the outer member 11 comprises a proximal hub 20, an elongate tube 21 extending distally and fixedly from the hub 20, and a tip 22 fixed to and extending distally of the tube 21. The tube 21 may be angled as here shown (e.g. bent or curved) or straight as desired.

The inner member 12 (FIG. 4) comprises a hub 30, an elongate shaft 31 fixed to and extending distally from the hub 30, and a tip 32 fixed to and extending forward from the shaft 31. It is contemplated that the shaft 31 may be solid or non tubular in some instances. However, in the preferred embodiment shown, the shaft 31 is tubular, as shown.

As schematically indicated in FIG. 1, the surgical instrument 10 may, for use, be fitted to a powered surgical handpiece HP, wherein the hub 20 is fixed to the handpiece housing H and the hub 30 is movably driven by a handpiece drive D, for example rotatably as here shown, or in some other way e.g. reciprocable.

The outer and inner tips 22 and 32 in the particular shaver type surgical instrument 10 shown in FIGS. 1-4 are normally located one outside the other and have rotatingly registering cutting windows 40 and 41, respectively, whose sharp cutting edges (here both toothed) mesh in shearing fashion to shear bits of tissue from a patient's surgical site schematically indicated at SS in FIG. 1. Such toothed shearing edges are respectively indicated at 42 and 43 in FIGS. 3 and 4.

Figure 4:
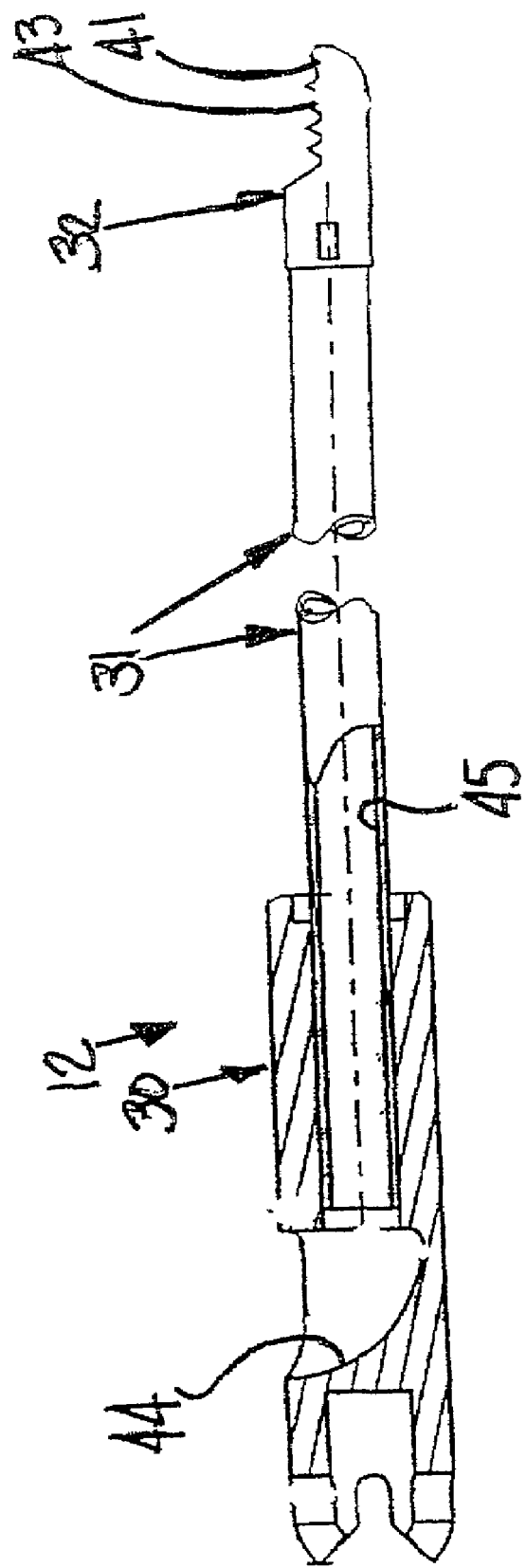
FIG. 4 is an enlarged, partially broken, fragmentary, elevational view of the inner member of the FIG. 1 instrument.

As indicated in FIGS. 1 and 4, the shaft 31 is preferably formed as an elongate tube communicating through a hollow proximal end of the tip 32 with the cutting window 41 and communicating its distal end through a port 44 in the drive hub 30 with a conventional suction source S (FIG. 1). Thus, liquid and solid particles can be suctioned through the cutting window 41, the interior passage 45 (FIG. 4) of the tubular shaft 31, the port 44 and the hub 30 and thence to the suction source S to remove same from the surgical site SS (FIG. 1).

At least one of the tube 21 and tubular shaft 31 is of a material deformable when heated e.g. a thermoplastic material, with the corresponding tip 40 and/or 41 being of a rigid material capable of holding a cutting edge, e.g. stainless steel. Such deformable material may be relatively stiff in its normal, unheated state where used for the tube 21 of the outer member 11 (whether straight or bent), or where used for the tubular shaft 31 of the inner member 12 where same is not required to bend or flex in use, as when the corresponding surrounding outer tube 21 is straight. However, when the corresponding outer tube 21 is bent as shown in FIG. 1, the moving inner tubular shaft 31 must be sufficiently flexible as to be capable of reciprocating (or as here rotating) within the bent outer tube 21. In that instance, a rotating inner tubular shaft 31 is conveniently of a thermoplastic material sufficiently flexible as to allow rotation within the bent outer tube 21.

To the extent above discussed, the apparatus of FIGS. 1-4 is conventional.

Turning now to the aspects of the disclosed apparatus more specifically embodying the invention, attention is directed to FIGS. 5-19. Whereas FIGS. 5-10 here disclose the invention applied to the shaft 31 and tip 32 of the inner member 12, it will be understood that same could be applied as well to the tube 21 and tip 22 of the outer member 11.

Turning now more specifically to FIGS. 5-10, the tip 32 has a generally tubular proximal end portion 50 having outer and inner peripheral surfaces 51 and 52. A projection or connector element 60 protrudes from a peripheral surface (here the inner peripheral surface 52) of the tip proximal portion 50 into the tip 32 adjacent the proximal (leftward in FIG. 7) end. The circumferential width WP of the projection preferably is substantially less than the circumferential width WS (FIG. 6) of the circumferential space between adjacent projections 60. Plural ones (for example four as here shown) of such projections 60 are preferably circumferentially distributed, here evenly, on the tip 32. The projection 60 here shown is elongated in a direction generally parallel to the longitudinal axis of the tip 32. The projection 60 is spaced axially inboard of the proximal end 53 of the tip 32.

The projection 60 may, within the scope of the invention, take various forms. For example, projections of various shapes (e.g. generally triangular, rectangular, multi-sided, round or oval) are contemplated, as are projections with one, two or more perimeter portions or the entire perimeter thereof attached to the adjacent part of the tip. Further, projections with or without openings are contemplated, as are projections of constant or varying thickness or cross-section.

Figure 8:
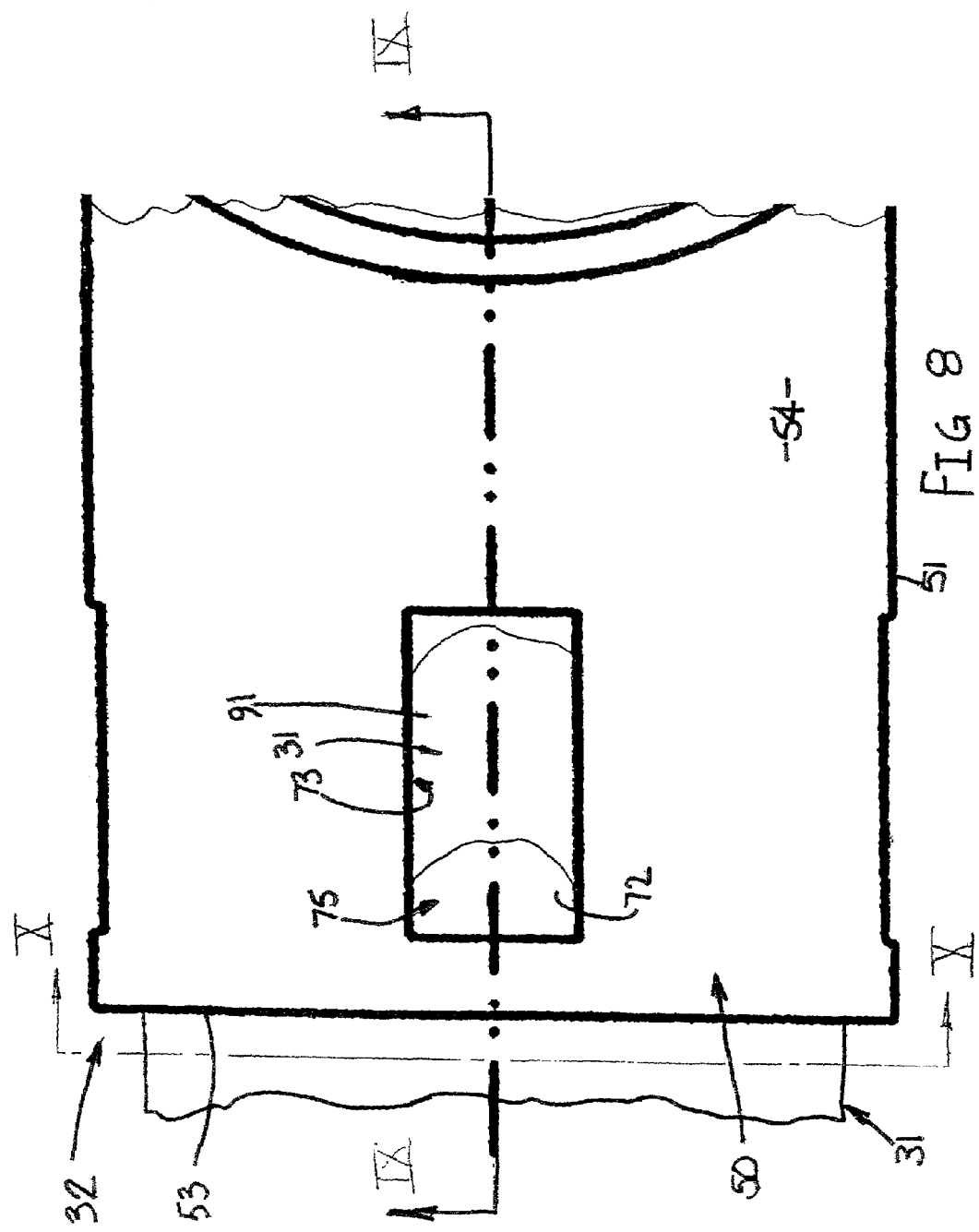
FIG. 8 is an enlarged fragment of FIG. 5 with the shaft of FIG. 4 assembled thereto.
Figure 9:
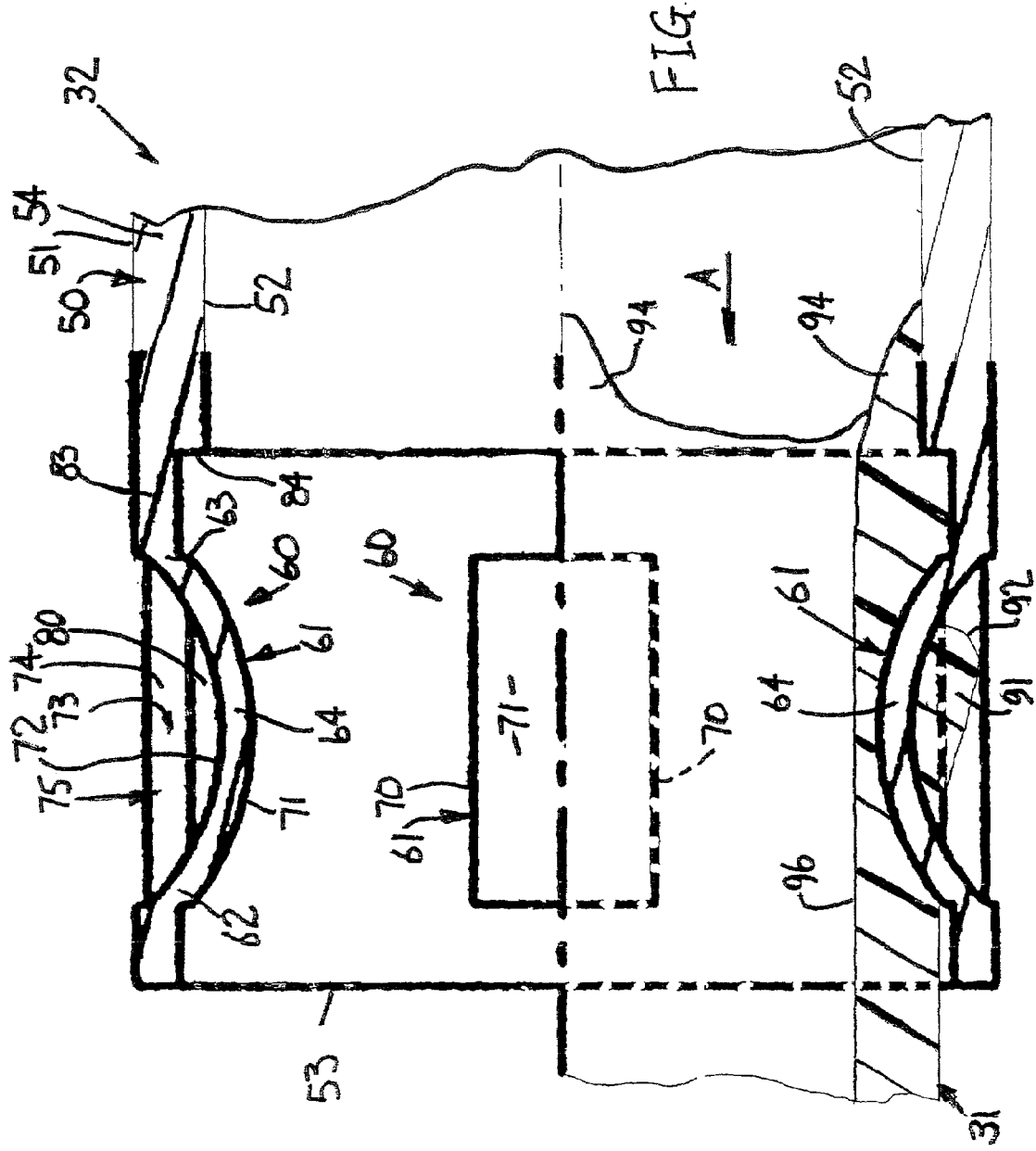
FIG. 9 is a partially broken, central cross sectional view substantially taken on the line IX-IX of FIG. 8.
Figure 10:
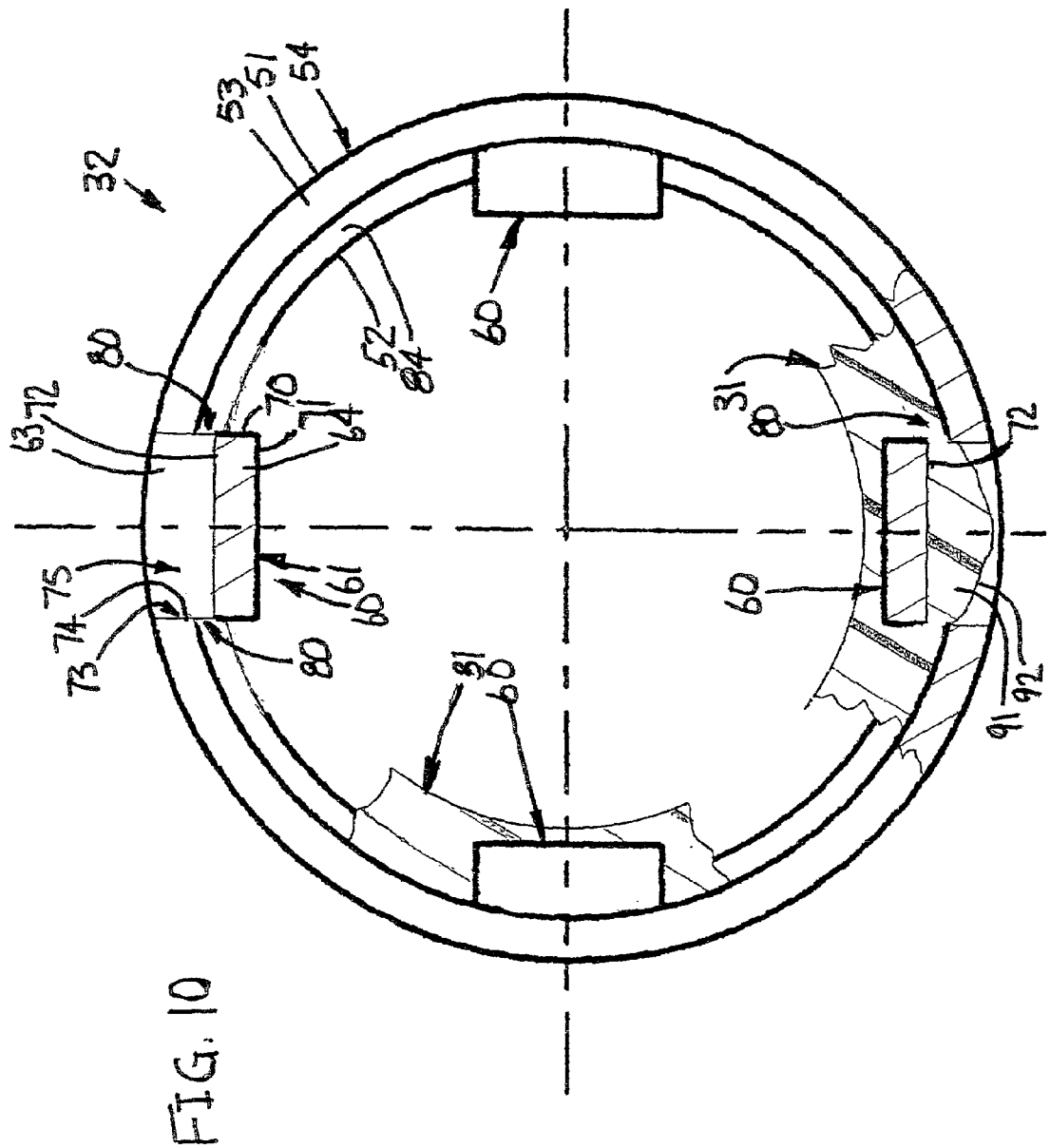
FIG. 10 is a partially broken cross sectional view substantially taken on the line X-X of FIG. 8.
Figure 11:
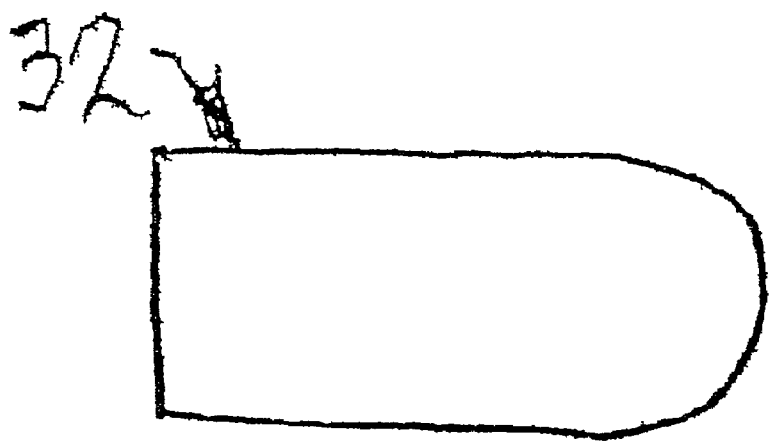
FIG. 11 is a schematic elevational view of the FIG. 4 tip in a stage of manufacture prior to providing the projections of FIGS. 5-7.
Figure 12:
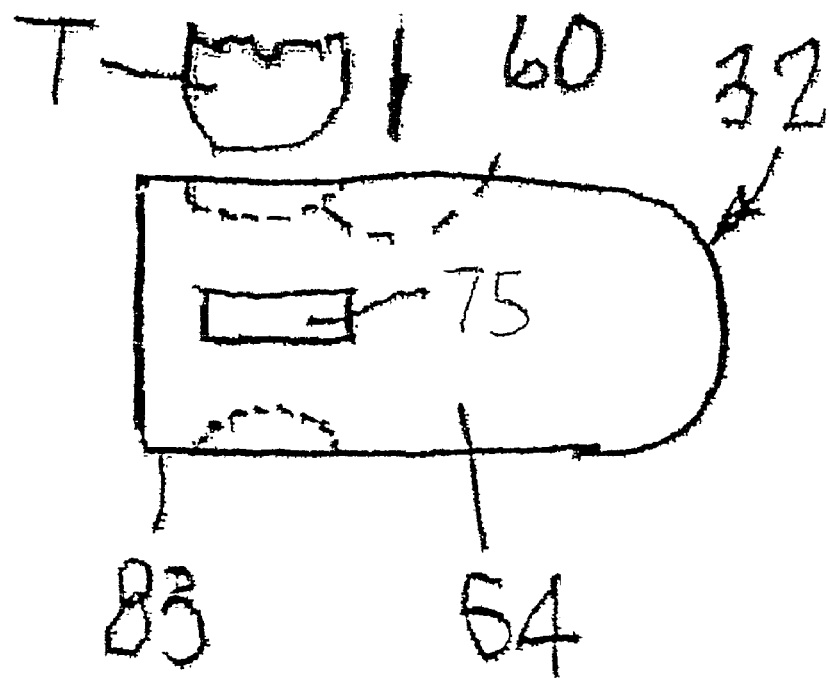
FIG. 12 schematically illustrates a method of forming the FIGS. 5-7 projections in the FIG. 11 tip.

However, in the preferred embodiment shown in FIGS. 8-10, and particularly as seen in FIG. 9, the projection 60 comprises a shallow C-shaped, rigid strip 61 having proximal and distal end portions 62 and 63, respectively, fixedly joining the tip proximal portion 50. The strip 61 has a central portion 64 extending radially from the generally tubular peripheral wall 54 of the tip peripheral portion 50. As seen looking radially in FIG. 9, the strip 61 is axially elongate and substantially rectangular in form. The FIG. 9 strip 64 is of substantially constant cross section throughout its length, and has side edges 70 and radially oppositely facing convex and concave faces connecting the side edges 70.

The projection 60, including the strip 61 (FIGS. 9 and 10), radially opposes a similarly shaped hole 73 in the tubular peripheral wall 54 of the tip proximal portion 50. The hole 73 has axially extending side edges 74 substantially radially aligned with the side edges 70 of the strip 61. The strip concave surface 72 and the side edges 74 of the hole 73 together may be said to define a depression generally indicated at 75 and which is complementary in cross section to the projection 61.

In the preferred embodiment shown, the central portion 64 of the strip 61 projects radially sufficient to form at least one opening 80, and here a circumferential opposed pair of openings 80 (FIGS. 9 and 10), substantially radially bounded by the strip side edges 70 and radially adjacent hole side edges 74. In conformance with the central cross sectional shape of the strip 64, the openings 80 (FIG. 9) are here of generally chordal shape. The openings 80 thus communicate the interior of the tip proximal portion 50 with the exterior of the proximal portion 50 at the projection 60 and the depression 75.

In the finished inner member 12 (FIG. 4), the hollow tubular shaft 31 and tip 32 are axially telescoped. It is contemplated that the tube 31 may in some instances be desirably telescoped over the proximal end of the tip 32, in which case it is desirable that the projection 61 project radially outwardly from the outer surface 51 of the proximal portion 50 of the tip 32, mainly in a radial direction opposite to that shown in the preferred embodiment of FIG. 9. However, in the preferred embodiment of FIG. 9, the hollow tubular shaft 31 is to be telescoped within the tube proximal end portion 50 of the tip 32, as hereafter described, such that the projection 61 extends radially inward into the generally cylindrical interior of the tip 32.

To reduce the radial thickness of the inner member 12 at the telescoped overlap of the hollow tubular shaft 31 and tip 32, and in view of the greater strength of a metal (e.g. surgical stainless steel) tip 32, as compared to a hollow tubular shaft 31 of possibly less strong material, e.g. a suitable plastic material, the rearmost part 83 of the tip proximal portion 50 may be reduced in thickness from that of the more distal portion of the tubular peripheral wall (at the reference numeral) 54 by means of an annular radial step 84 (FIG. 9). Such a step would normally appear in the outer peripheral surface 51 of the tip 32 in embodiments where the hollow tubular shaft 31 is telescoped over the proximal end of the tip 32. However, in the preferred embodiment shown, the annular radial step 84 is in the inner peripheral surface 52 of the tip proximal portion 50, to provide enough radial clearance to allow the distal end portion of a shaft 31 to be telescoped within the tip proximal portion 50, as hereafter discussed.

In the embodiment shown, the hollow tubular shaft 31 (FIGS. 8-10) is of suitable thermoplastic material, e.g. an acetal polymer or polyoxymethylene, although Applicant contemplates the use of other plastic materials such as polyetherimide, polysulfone, nylon, polyimide, urethane, polyether block amide and polytetrafluoroethylene (PTFE).

The shaft 31 may be substantially rigid in surgical instruments 10 of the kind having a substantially straight outer member 11. However, where the inner member 12 is to move (e.g. rotate) in an outer member 11 (FIG. 1) having an angled tube 21, the tubular shaft 31, at least in a region of such bend, must be sufficiently flexible to allow it to drive (e.g. rotatably) the tip 32 within the tip 22 of the outer member 11. In that instance, the hollow tubular shaft 31 may be of a suitable reinforced or non-reinforced thermoplastic material.

Figure 13:
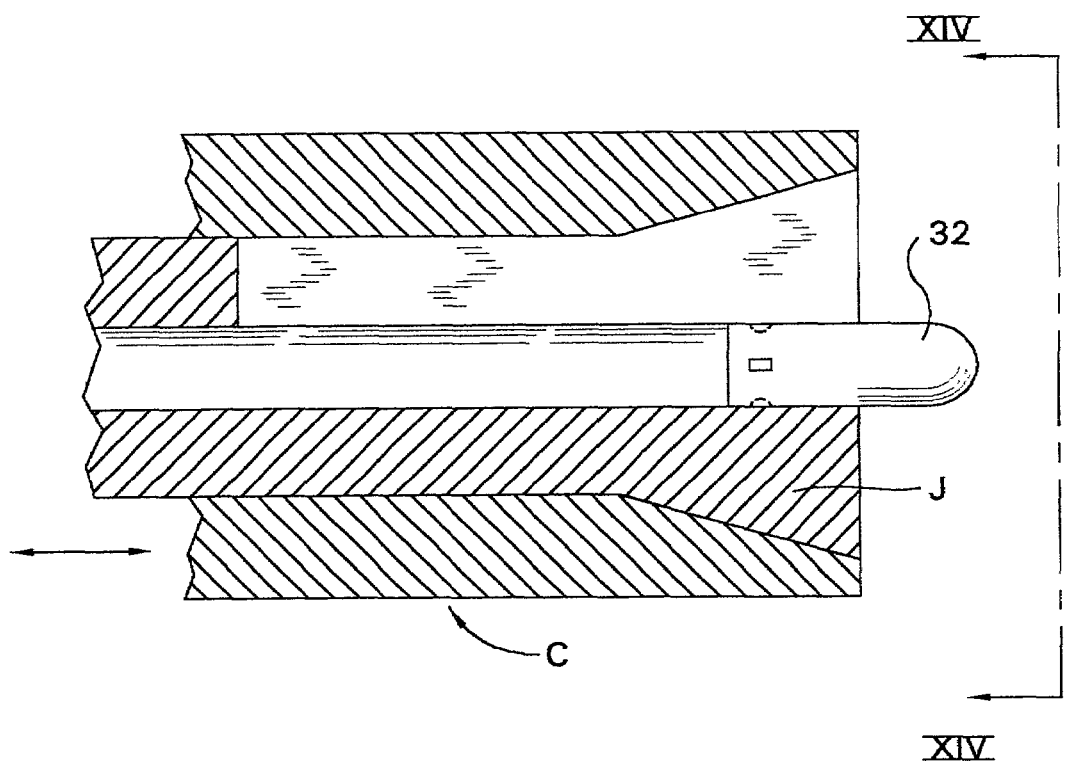
FIG. 13 schematically illustrates the use of a tool on the tip to assure circularity of the tip following the FIG. 12 formation of depressions therein.
Figure 14:
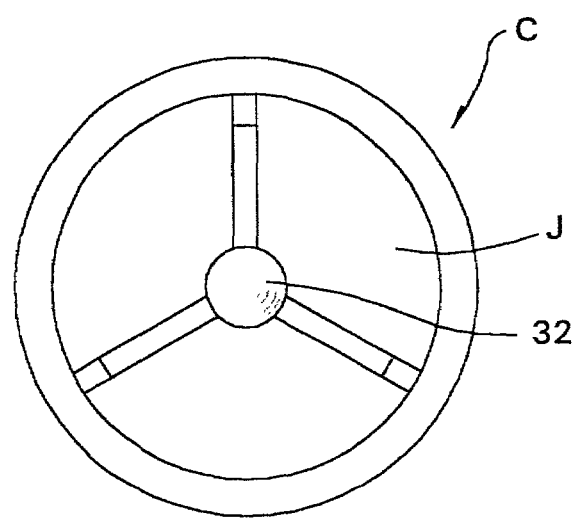
FIG. 14 is an end elevational view substantially taken on the line XIV-XIV of FIG. 13.
Figure 15:
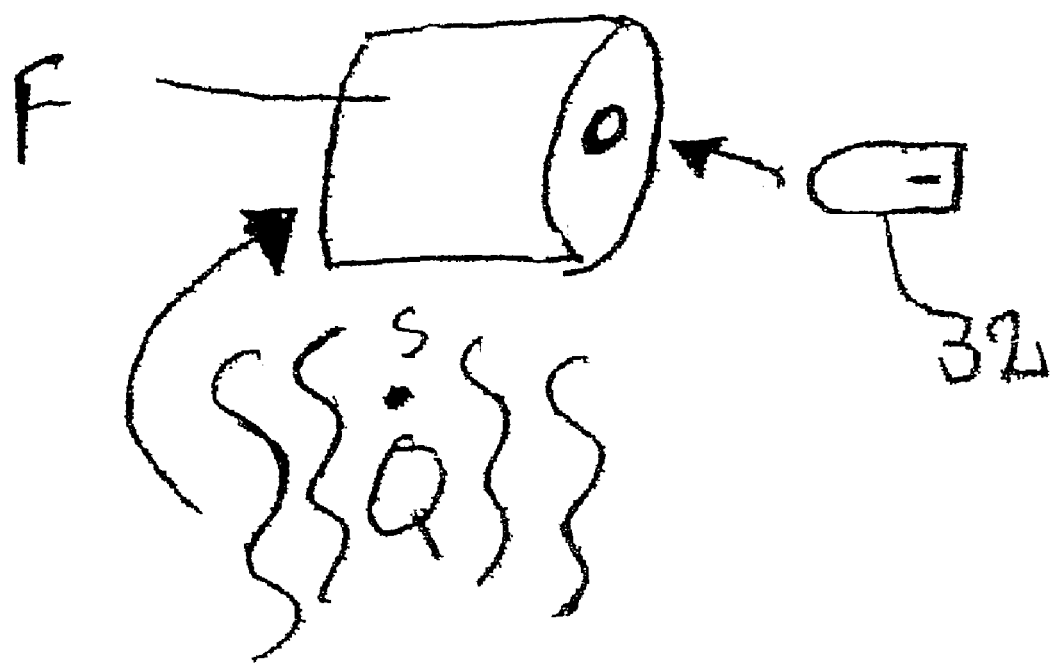
FIG. 15 schematically shows the insertion of the FIG. 13 tip into a heating fixture.
Figure 16:
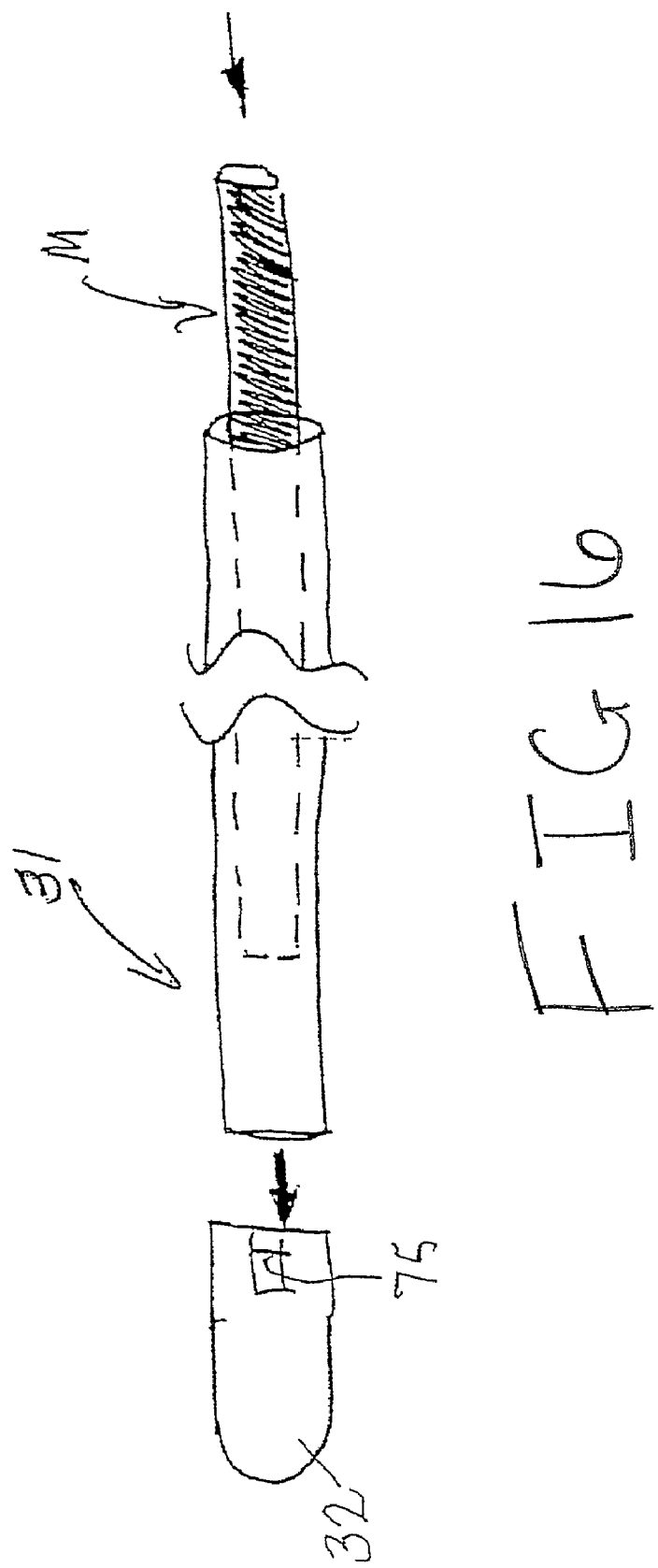
FIG. 16 schematically shows the insertion of a mandrel into the FIG. 4 hollow shaft prior to insertion of the latter into the heated tip.
Figure 17:
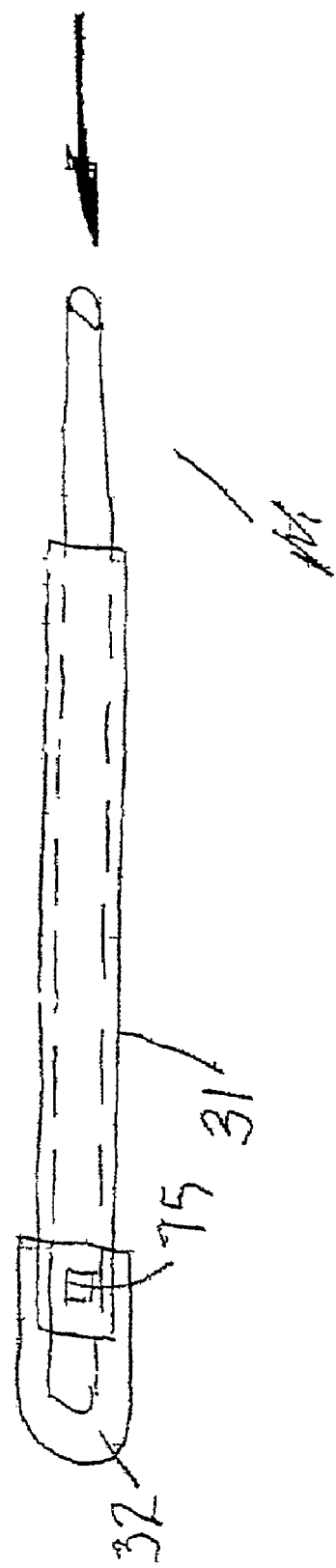
FIG. 17 schematically shows the mentioned hollow shaft, backed by the mandrel and inserted into the open proximal end of the heated tip.

FIGS. 11-19 schematically portray a preferred method for fixedly joining the hollow tubular shaft 31 and tip 32. For convenience, above discussed structural details not central to this method, such as the cutting window in the tip 13, are not shown, but will be understood to be present. The tip 32 is first manufactured (FIG. 11), except for the projections 60 and depressions 75. A lancing tool T (FIG. 12) is driven radially into the rearmost part 83 of the tip peripheral wall 54 to form the corresponding depressions 75 and projections 60. This may be done either using one tool T or simultaneously using a number of circumferentially spaced tools T corresponding to the number of projections 60 to be formed. Any deviation from tip circularity which may result from the lancing operation is corrected by chucking the proximal end of the tip in the jaws J of a precision collet C (FIGS. 13 and 14). The tip 32 is then inserted into a fixture F (FIG. 15) wherein the tip 32 is heated. An elongate mandrel M (FIG. 16) is partially inserted into the proximal end of the hollow tubular thermoplastic shaft 31 and the distal end of the latter is then inserted into the proximal end of the heated tip 32. After the hollow tubular thermoplastic shaft 31 is inside the heated tip 32, the mandrel M (FIG. 17) is inserted further into the shaft 31 to force the now warmed and flowable plastic material of the hollow tubular shaft 31 outwardly into engagement with the projections 60 and into the depressions 75. It will be understood that the tip 32 continues fixed in place in the fixture F (FIG. 15) throughout the FIGS. 16 and 17 steps. Thereafter, the assembly, comprising the tip 32 and hollow tubular shaft 31 and mandrel M, is moved away from the heating fixture F (as seen in FIG. 18) and allowed to cool, to fixedly connect the tip 32 to the hollow tubular shaft 31. After the assembled tip 32 and hollow tubular shaft 31 (FIG. 19) have cooled, the mandrel M is removed proximally from the shaft 31.

The above described method may be used to fixedly join a non tubular (e.g. solid) shaft (not shown) to the tip 32, in which case the mandrel M would generally be omitted.

After the aforementioned cooling, any thermoplastic material from the shaft 31 that has extruded radially outwardly from the recesses 75 (considered "flash") is removed, so that the outer perimeter of the tip 32 at the recesses 75 is flush (or at least does not extend radially outward beyond) the remainder of the outer peripheral surface 51 of the tip 32.

The resultant fixed connection of the tip 32 on the distal end of the hollow tubular shaft 31 is indicated in FIGS. 8-10. More particularly, it will be seen that material of the hollow tubular thermoplastic shaft 31 has flowed forward past the projections 60 with a portion or finger 91 of such material having flowed circumferentially through the openings 80 and in a claw-like manner onto the concave surface 72 of the projections 60. The flow may be sufficient to cause such material 91 to form a bridge 92 circumferentially across the concave surface 72 of the projection 60, so as to encapsulate the central portion 64 of the projection 60 and hence the strap 64.

However, it will be understood that a sufficiently strong connection of the tip 32 to the shaft 31 is provided by the axial and circumferential surrounding of the projection 60 by the material of the shaft 31 (i.e. the protrusion of the projection 60 into the material of the shaft 31) and does not depend on the aforementioned flow of shaft material through the openings 80, or on a deposit of shaft material on the concave surface 72 in a clawlike or bridging manner, as in FIG. 8.

Displacement of portions of the thermoplastic material of the tubular shaft 31, around the protrusions 61, may result in some flow of thermoplastic material distally slightly beyond the step 84, to form forward extensions 94 of forwardly diminishing thickness and which tend to converge in a generally smoothly tapering manner against the tip inner peripheral surface 52, to minimize impediment to suction flow proximally from a surgical site SS generally in the direction of arrow A (FIG. 9).

As seen in FIGS. 9 and 10, the flowed thermoplastic material of the tubular shaft 31 fills the circumferential space between adjacent protrusions 60. The relative circumferential width, of a protrusion 60 and the space between the latter and an adjacent protrusion 60, may be varied. However, as hereafter discussed, it is preferred that the circumferential extent of tubular shaft thermoplastic material circumferentially between protrusions 60 is substantially wider circumferentially than the protrusions 60 themselves. Given that the thermoplastic material of the tubular shaft 31 is typically less strong (e.g. shear resistant) than the metal (preferably surgical stainless steel) of the protrusions 60, the substantially greater circumferential width of thermoplastic material between protrusions 60, as compared to the circumferential width of the protrusions 60, maximizes the torque resistance of the connection between the tubular shaft 31 and tip 32. Indeed, making the axial length L of the protrusions 60 greater than their circumferential width WP (FIG. 5) increases the circumferential contact area between the thermoplastic material of the tubular shaft 31 and the protrusions 60 to further enhance torque resistance of the connection between the tip and tubular shaft.

Also, the above discussed minimizing of the circumferential width of the protrusions 60, and spacing of the protrusions 60 forward from the tip rear end 53, strengthens the reduced thickness, rearwardmost part 83 of the tip 32 against radial crushing from its preferred circular (except for the protrusions 60) shape. Telescoping of the distal end portion of the tubular shaft 31 into the rearmost portion 83 of the tip 32, with the radial backing of the mandrel M above discussed, snugly radially backs the peripheral wall of the rearwardmost tip portion 83 with eventually hardened thermoplastic material of wall thickness substantially exceeding that of the tip rearwardmost portion 83, and thereby further strengthens, against radial crushing, the tip rearward portion 83.

The above discussed interengagement of thermoplastic material of the tubular shaft 31 with the tip protrusions 60, which provides torque resistance therebetween, will be seen (FIG. 9) to positively lock the tubular shaft 31 and tip 32 against axial separation forces and axial compression forces.

The protrusion 60 preferably extends radially almost through the peripheral wall of the tubular shaft 31, again to maximize contact circumferentially and axially between the tip 32 and tubular shaft 31. Whereas the central portion 64 of a protrusion 60 may extend fully through such peripheral wall to the opposite side (the interior side in FIG. 9) thereof, the protrusion 60 preferably does not extend radially past the far surface 96 (inner peripheral surface in FIG. 9) of the tubular shaft 31, such that the latter surface 96 preferably remains smooth and substantially unbroken, again to facilitate suction flow, in the direction of the arrow A, from the surgical site SS.

As mentioned, the tip projections may be formed without openings (e.g. openings 80 of FIG. 9). For example, a relatively small diameter instrument (e.g. a 3 mm or less outside diameter cutter) may have an inner tubular shaft, and corresponding tip projections extending radially thereinto, of such little radial extent that formation of the projections by lancing does not rupture the tip peripheral wall. Indeed, where the lance penetrates less than the radial wall thickness of the tip, it will normally form a projection without a corresponding opening or openings.

Although a particular preferred embodiment of the invention has been disclosed in detail for illustrative purposes, it will be recognized that variations or modifications of the disclosed apparatus, including the rearrangement of parts, lie within the scope of the present invention.

We claim:

1. A surgical instrument of the kind having a hand piece engagable proximal part and a tissue working distal part, said surgical instrument comprising:
   an outer member;
   an inner member movable in said outer member;
   at least one said member comprising:
      a proximal member having a generally tubular distal portion; and
      a tissue working tip having a generally tubular proximal portion, said tip proximal portion and proximal member distal portion being at least partly telescoped and therewith having radially opposed surfaces, said tip proximal portion having a plurality of circumferentially-spaced projections generally protruding from said surface of said tip, a circumferential space defined between adjacent ones of said projections being circumferentially wider than an adjacent said projection, said radially opposed surface of said proximal member having portions disposed in locations corresponding with said projections, a substantial part of each said portion being disposed in superimposed relation with the corresponding said projection and thereby relatively fixing said proximal member and said tip.

2. The instrument of claim 1 in which said projections are embedded in said proximal member.

3. The instrument of claim 1 in which each said projection is elongated in a direction generally parallel to a longitudinal axis of said tip, such that the axial length of each said projection exceeds its circumferential width.

4. The instrument of claim 1 in which the radial extent of each said projection approximates a radial wall thickness of said proximal member distal portion.

5. The instrument of claim 4 in which said radial extent of each said projection is less than said radial wall thickness of said proximal member distal portion, so as to protrude through only one surface of said proximal member distal portion.

6. The instrument of claim 1 in which said one member comprises said inner member.

7. The instrument of claim 1 in which said one member comprises said outer member.

8. The instrument of claim 1 in which said proximal member distal portion extends into the proximal end of said tip, said projections extending into the interior of said tip and into the material of said proximal member.

9. The instrument of claim 1 in which said proximal portion of said tip extends into said proximal member distal portion, said projections extending outward of said tip into the material of said proximal member distal portion.

10. The instrument of claim 1 in which said tip is of metal and said proximal member is of a thermoplastic material.

11. The instrument of claim 1 in which said proximal member is of a thermoplastic material selected from the group consisting of acetal polymer, polyoxymethylene, polyetherimide, polysulfone, nylon, polyimide, urethane, polyether block amide and polytetrafluoroethylene.

12. The instrument of claim 11 in which said proximal member is of an acetal polymer.

13. A surgical instrument comprising:
an outer member fixable on a powered hand piece;
an inner member movably disposed in said outer member and drivingly engagable with a hand piece motive power source;
at least one said member comprising a proximal member having a distal portion and a tip having a generally tubular proximal portion, said tip proximal portion comprising a wall having an inner peripheral surface and an outer peripheral surface, a projection protruding from one said peripheral surface, said projection defining a strip having opposite ends integral with said tip proximal portion and an intermediate portion bent away from said ends, the other said peripheral surface having a depression backing said projection.

14. The instrument of claim 13 in which said projection and depression together define a lancing artifact.

15. The instrument of claim 13 including an opening through said wall at said projection and which directly communicates said projection with said depression.

16. The instrument of claim 15 in which material of said proximal member extends through said opening into said depression and at least partially fills said depression.

17. The instrument of claim 16 in which said strip defines said depression and projection, at least a portion of said strip being sandwiched by material of said proximal member.

18. The instrument of claim 15 in which said opening separates a portion of said strip from the rest of said one peripheral surface.

19. The instrument of claim 18 including a pair of said openings through opposite sides of said strip.

20. The instrument of claim 19 in which material of said proximal member engages said projection, with fingers of said material extending through said openings toward each other at least partly across said strip and thereby gripping said strip in a generally claw-like manner.

21. A surgical instrument comprising an outer generally elongate and tubular member configured for attachment to a powered handpiece, an inner generally elongate member movably disposed within said outer member and configured for being driven by a power source associated with a handpiece, one of said members comprising a proximal portion and a distal tip portion defining a cutting edge thereon, said distal tip portion having a proximal end having inner and outer surfaces and defining therein an opening which extends through said proximal end between said inner and outer surfaces, said proximal portion having a distal end part which projects into said opening and engages both said inner and outer surfaces to interlock said distal tip portion and said proximal portion to one another.

22. The surgical instrument of claim 21, wherein said proximal portion has a length which is substantially greater than a length of said distal tip portion.

23. The surgical instrument of claim 21, wherein a plurality of said openings are disposed in a spaced-apart manner about said proximal end of said distal tip portion, and said proximal portion defines a plurality of said distal end parts interlockingly engaged in corresponding ones of said openings.

24. The surgical instrument of claim 21, wherein said one member defines a central longitudinal axis, said proximal end of said distal tip portion defining thereon a radially-extending projection, said projection being defined by a strip of material deformed from said proximal end and defining part of said outer surface and part of said inner surface engaged by said distal end part, said opening being disposed immediately adjacent said strip.

25. The surgical instrument of claim 24, wherein said strip includes a pair of axially-spaced ends connected to and integral with said distal tip portion, and an intermediate section disposed axially between, but radially spaced from, said ends.

26. The surgical instrument of claim 25, wherein said proximal end of said distal tip portion defines a pair of said openings therein on opposite sides of said strip, said strip projecting radially inwardly from said distal tip portion.

27. The surgical instrument of claim 21, wherein said proximal portion is disposed within said proximal end of said distal tip portion in a telescoping manner.

28. A surgical apparatus comprising:
an outer generally hollow tubular shaft defining a central longitudinal axis and being configured for attachment to a surgical handpiece;
an inner shaft movably disposed within said outer shaft and configured for being driven by a power source associated with a surgical handpiece, said inner shaft defining a cutting edge thereon; and
one of said shafts including an elongate proximal portion and a distal end portion, said distal end portion defining on a surface thereof a plurality of circumferentially-spaced and radially-projecting connector elements, each said connector element defining a strip having opposite axial ends integral with said distal end portion and an intermediate portion bent away from said ends, each said connector element being surrounded by a generally projectionless surface area of said distal end portion substantially greater than a distal end portion surface area occupied by each said connector element, and each said connector element being engaged with corresponding portions of a distal end of said proximal portion so as to fixedly interconnect said proximal portion and said distal end portion to one another.

29. The surgical apparatus of claim 28, wherein said proximal portion is constructed of a first material and said distal end portion is constructed of a second material different from said first material.

30. The surgical apparatus of claim 29, wherein said second material, is metal and said first material is plastic.

31. The surgical apparatus of claim 28, wherein said proximal portion has a flexible portion disposed along a length thereof.

32. A surgical apparatus comprising:
an elongate outer and generally tubular shaft defining a central longitudinal axis, said outer shaft having a proximal end configured for attachment to a powered surgical handpiece, a distal end spaced from said proximal end and defining a cutting window therein, and an intermediate portion disposed between said proximal and distal ends; and
an elongate inner and generally tubular shaft having a proximal end configured for being driven by a drive of a powered handpiece, a distal end defining a cutting window therein, and an intermediate portion disposed between said inner shaft proximal and distal ends, said inner shaft being movably disposed within said outer shaft such that said cutting windows are disposed axially adjacent one another, one of said distal ends being constructed of a first material and one of said intermediate portions corresponding to said one distal end being constructed of a second material different from said first material, said one distal end being deformed so as to define a radially projecting strip having a part which is separated from said one distal end, said one intermediate portion having a length greater than a length of said one distal end and engaging said radially-deformed strip so as to fixedly interconnect said one distal end and said one intermediate portion.

33. The apparatus of claim 32, wherein said inner shaft comprises said one distal end and said one intermediate portion, said first material being rigid and said second material being flexible to allow bending of said inner shaft in a direction transverse to the longitudinal axis.

34. The apparatus of claim 32, wherein said outer shaft comprises said one distal end and said one intermediate portion.

35. The apparatus of claim 32, wherein a distal end of said one intermediate portion and a proximal end of said one distal end are disposed in telescoping relation with one another.

36. The apparatus of claim 35, wherein said distal end of said one intermediate portion is disposed within said proximal end of said one distal end and projects into said separated part of said strip, said separated part defining an opening which extends through said one distal end.

37. A surgical instrument comprising an elongate shaft defining a longitudinal axis, said shaft having a proximal end configured for being driven by a powered surgical handpiece, a distal end portion spaced from said proximal end and defining a cutting edge thereon, and an intermediate portion disposed between said proximal and distal ends, said intermediate portion being constructed of a first material and said distal end portion being constructed of a second material different from said first material, said distal end portion being deformed so as to define thereon a radially-projecting part which is partially separated from said distal end portion to define an opening extending through said distal end portion, said intermediate portion having a part extending into said opening and around an edge of said radially-projecting part so as to engage opposite sides thereof and fix said intermediate portion and said distal end portion together.

* * * * *